(12) United States Patent
Kim

(10) Patent No.: US 11,883,249 B2
(45) Date of Patent: Jan. 30, 2024

(54) TOOTH SEPARATION SYSTEMS AND METHODS

(71) Applicant: 3D Industrial Imaging Co., Ltd., Seoul (KR)

(72) Inventor: Seung Ki Kim, Seoul (KR)

(73) Assignee: 3D Industrial Imaging Co., Ltd., Seoul (KR)

( * ) Notice: Subject to any disclaimer, the term of this patent is extended or adjusted under 35 U.S.C. 154(b) by 511 days.

(21) Appl. No.: 17/270,091

(22) PCT Filed: Aug. 23, 2019

(86) PCT No.: PCT/KR2019/010751
§ 371 (c)(1),
(2) Date: Feb. 22, 2021

(87) PCT Pub. No.: WO2020/040588
PCT Pub. Date: Feb. 27, 2020

(65) Prior Publication Data
US 2021/0205057 A1    Jul. 8, 2021

(30) Foreign Application Priority Data
Aug. 23, 2018 (KR) .................. 10-2018-0098286

(51) Int. Cl.
*A61C 13/00* (2006.01)
*G06T 7/10* (2017.01)
(Continued)

(52) U.S. Cl.
CPC ........ *A61C 13/0004* (2013.01); *A61C 9/0046* (2013.01); *A61C 13/34* (2013.01);
(Continued)

(58) Field of Classification Search
None
See application file for complete search history.

(56) References Cited

U.S. PATENT DOCUMENTS 8,923,581 B2   12/2014   Souza et al.
2005/0019732 A1*  1/2005  Kaufmann ............... G06T 7/12
                                                                433/213
(Continued)

FOREIGN PATENT DOCUMENTS

JP    2009-146178 A    7/2009
KR    10-2013-0044932 A    5/2013
(Continued)

OTHER PUBLICATIONS

International Search Report from corresponding PCT Application No. PCT/KR2019/010751, dated Dec. 26, 2019.

*Primary Examiner* — Jeffrey J Chow
(74) *Attorney, Agent, or Firm* — Harness, Dickey & Pierce, P.L.C.

(57) ABSTRACT

A tooth separation system comprising: a loading unit for loading an intraoral scan data; a display unit for displaying the intraoral scan data loaded by the loading unit, in which the intraoral scan data includes a tooth as well as gums; an input unit for making a tooth border mark onto the tooth shown on the display unit; and a calculation unit for performing necessary calculations to separate the tooth from the gums based on the tooth border mark and the method using the same.

7 Claims, 8 Drawing Sheets

(51) Int. Cl.
*A61C 9/00* (2006.01)
*A61C 13/34* (2006.01)
*G16H 50/50* (2018.01)
*G16H 30/40* (2018.01)

(52) U.S. Cl.
CPC .............. *G06T 7/10* (2017.01); *G16H 30/40* (2018.01); *G16H 50/50* (2018.01); *G06T 2207/30036* (2013.01)

(56) References Cited

U.S. PATENT DOCUMENTS

2008/0030497 A1   2/2008   Hu et al.
2019/0029522 A1*  1/2019   Sato ........................ G06T 15/08
2019/0152152 A1*  5/2019   O'Leary ................ B33Y 30/00
2021/0366119 A1* 11/2021   Salah ..................... G16H 50/20

FOREIGN PATENT DOCUMENTS

KR   10-2013-0105519 A   9/2013
KR   10-2018-0090308 A   8/2018
WO   WO-2017/093563 A1   6/2017

\* cited by examiner

Prior Art

TOOTH SEPARATION SYSTEMS AND METHODS

CROSS-REFERENCE TO RELATED APPLICATIONS

This application is a national phase application of PCT Application No. PCT/KR2019/010751, filed on Aug. 23, 2019, which claims priority to Korean Patent Application No. 10-2018-0098286, filed on Aug. 23, 2018. The entire disclosures of the applications identified in this paragraph are incorporated herein by references.

TECHNICAL FIELD

This disclosure relates generally to systems and methods for separating teeth from gums in image data and more particularly, to systems and methods for automatically separating teeth from gums in intraoral scan data of a patient obtained by a dental 3D scanner.

BACKGROUND

This section provides background information related to this disclosure which is not necessarily prior art.

In treatment of teeth, dental prostheses may need to be attached to teeth depending on the degree of damage to corresponding teeth. As each person has different tooth shapes, positions, and sizes, it is necessary to prepare a prosthesis that conforms with a unique shape of a tooth of the person being treated. In general, a dental CAD/CAM system is used to fabricate any dental prosthesis as needed in dental clinics or dentist's offices. First, a tooth, any suitable impression material, or a dental model made from such an impression material is scanned with a 3D dental scanner, and the resulting intraoral scan data is then used for the CAD/CAM system in preparation of a desired dental prosthesis. However, gums and teeth in the intraoral scan data are not separated, making it impossible to design a single-tooth prosthesis using the CAD/CAM system. Because of this, conventional CAD/CAM systems had adopted an algorithm in which tooth model data is generated such that teeth can be separated from gums in the intraoral scan data and processed individually. Once tooth model data is generated, a tooth prosthesis is designed based on the data in the dental CAD/CAM system, and then fabricated with a 3D printer.

FIG. 1 shows an exemplary dental CAD/CAM system available from 3Shape, Inc.

In this dental CAD/CAM system 10, a loading unit (not shown) loads dental CBCT (Cone Beam CT) scan data, which includes teeth 12 as well as gums 13 of a patient, and a display unit 11 shows these teeth and gums all together in three dimensions. Although the teeth 12 and the gums 13 appear to be distinguishable from each other on the display unit 11, they are not from the data, meaning that it was not possible to isolate a tooth 12 from the gum, as in FIG. 1D, for further processing in the dental CAD/CAM system 10. Therefore, 3Shape, Inc., has introduced a new algorithm in which a user clicks on two different points 14, 15 on each tooth 12 using an input unit such as a mouse, and a calculation unit (not shown) in the dental CAD/CAM system 10 automatically performs necessary calculations and draws a boundary line 16 on the display unit 11 for distinguishing the teeth 12 from the gums 13, as shown in FIG. 1C. Subsequently, tooth model data is generated from the intraoral scan data, which allows the user to process the teeth 12 individually on the display unit 11 in the system 10, as shown in FIG. 1D.

FIG. 2 shows another exemplary dental CAD/CAM system available from Exocad Gmbh.

In this dental CAD/CAM system 20, a loading unit (not shown) loads intraoral scan data which includes teeth 22 as well as gums 23 of a patient, and a display unit 21 shows these teeth and gums all together in three dimensions. With this dental CAD/CAM system, the user may simply click on any random point 24 between the teeth 12 and the gums 23, for distinguishing them automatically and obtaining tooth model data to be used in the system 20.

While the systems illustrates in FIGS. 1 and 2 allow the user to obtain tooth model data automatically by selecting one or more points on the image, it is often hard to get accurate tooth model data because the shapes and sizes of teeth vary greatly from one person to the other, and different types of teeth of a person also vary greatly in shapes and sizes. In addition, having the user select multiple points is not very convenient either.

Therefore, there is a need to develop systems and methods for separating teeth from gums in image data, such that accurate tooth model data can be automatically generated from intraoral scan data in a dental CAD/CAM system, increasing the convenience of users.

Technical Purpose

The purposes of this disclosure are described in the below.

SUMMARY

This section provides a general summary of the disclosure and is not a comprehensive disclosure of its full scope of all of its features.

According to one aspect of the present disclosure, there is provided a tooth separation system comprising: a loading unit for loading an intraoral scan data; a display unit for displaying the intraoral scan data loaded by the loading unit, in which the intraoral scan data includes a tooth as well as gums; an input unit for making a tooth border mark onto the tooth shown on the display unit; and a calculation unit for performing necessary calculations to separate the tooth from the gums based on the tooth border mark.

According to another aspect of the present disclosure, there is provided a tooth separation method comprising: loading, by a loading unit, an intraoral scan data; displaying, by a display unit, a tooth as well as gums according to the intraoral scan data; making, by an input unit, a tooth border mark onto the tooth shown on the display unit; and performing necessary calculations, by a calculation unit, so as to separate the tooth from the gums based on the tooth border marks.

Technical Effect

The purposes of this disclosure are described in the below.

DETAILED DESCRIPTION

The present disclosure will now be described in detail with reference to the accompanying drawing(s). It should be appreciated that the directional terms "upwards/downwards", "upper/lower", and derivatives thereof refer to orientations or directions with respect to corresponding drawings.

Figure 1A:
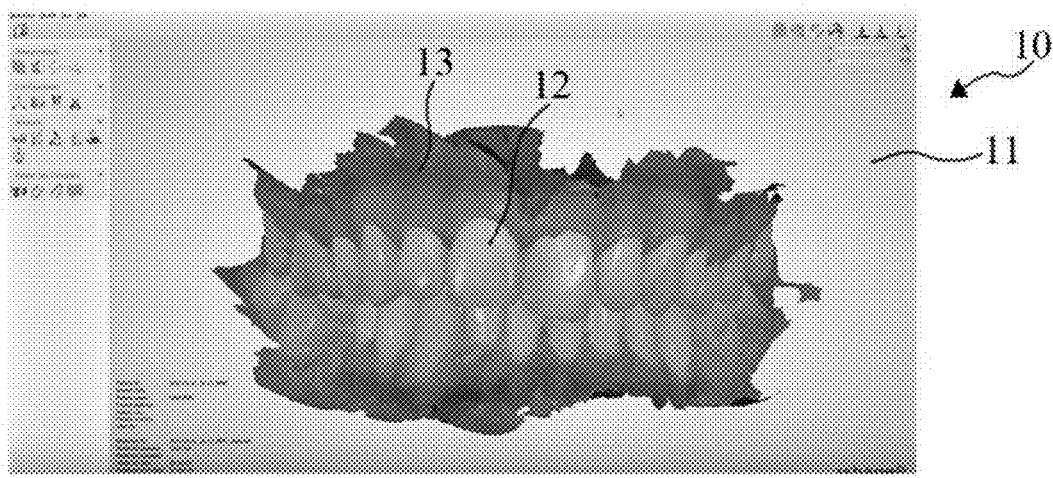
FIGS. 1A, 1B, 1C and 1D show an exemplary dental CAD/CAM system available from 3Shape, Inc.
Figure 1B:
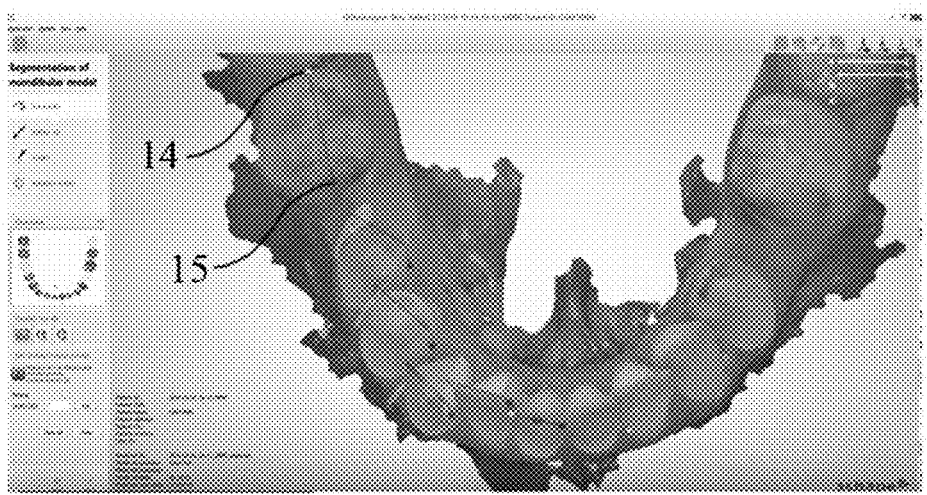
Figure 1C:
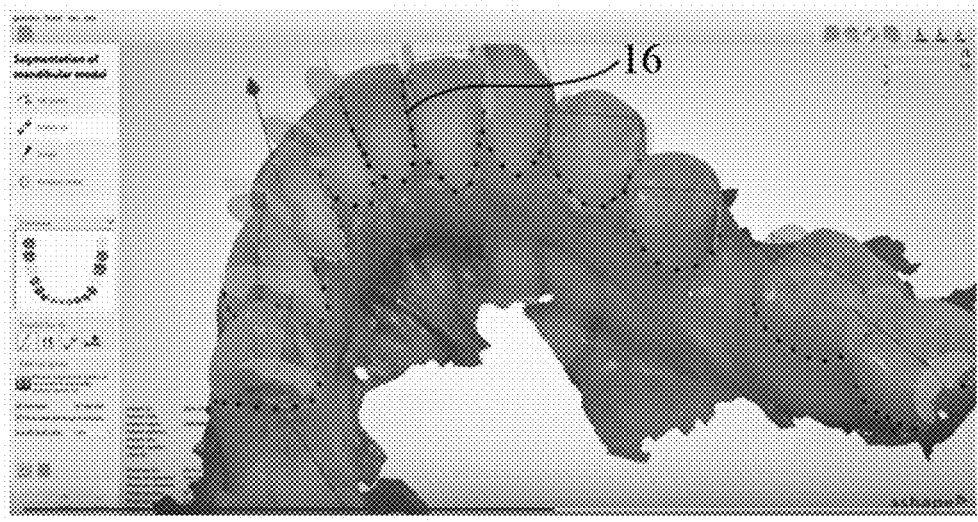
Figure 1D:
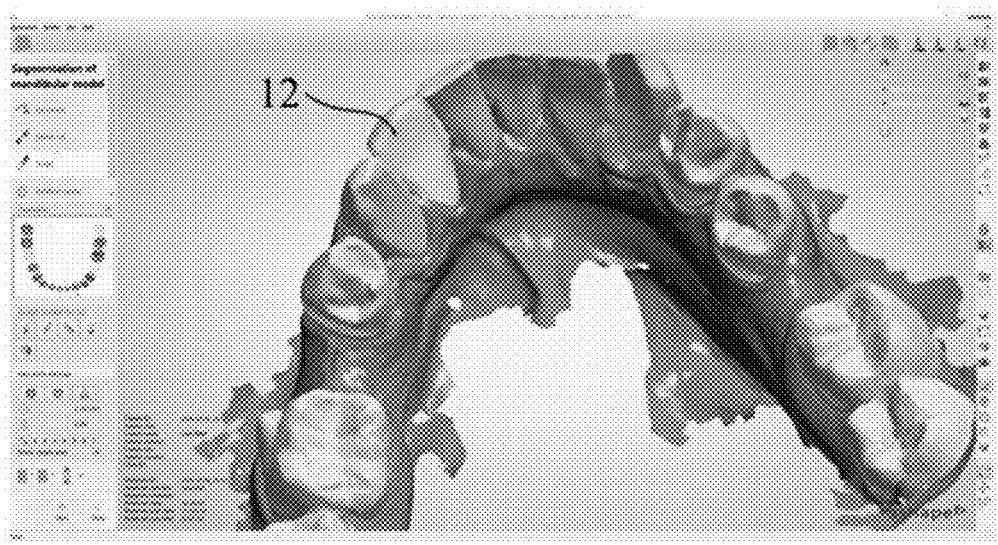
Figure 2:
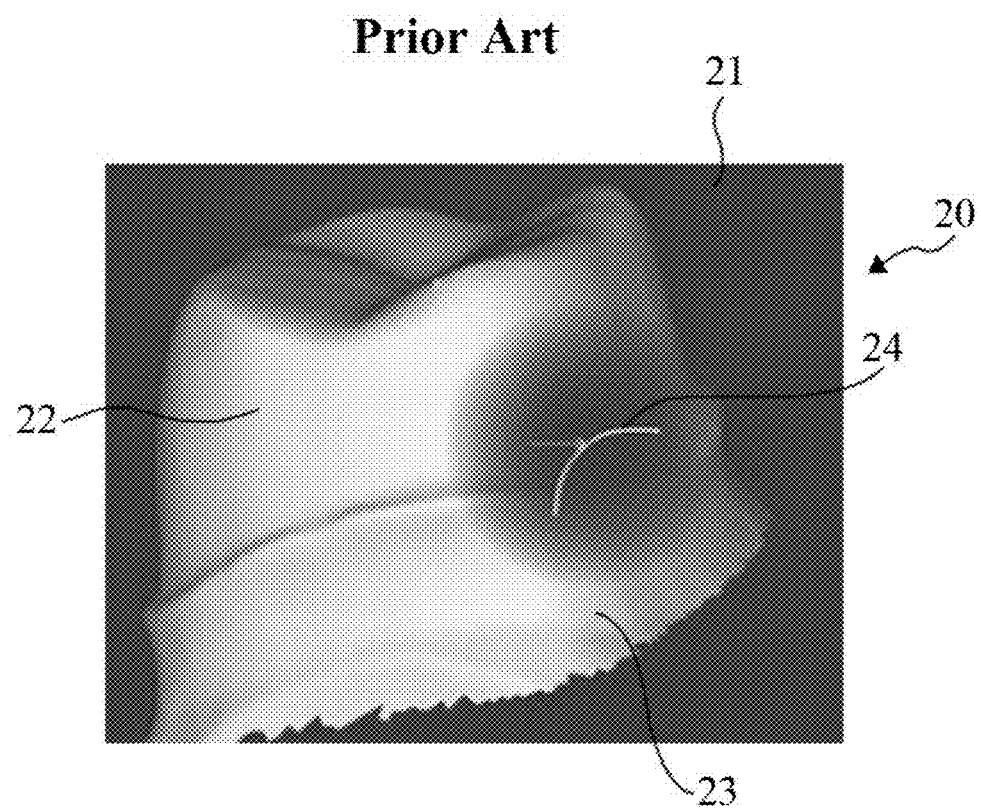
FIG. 2 shows another exemplary dental CAD/CAM system available from Exocad Gmbh.
Figure 3:
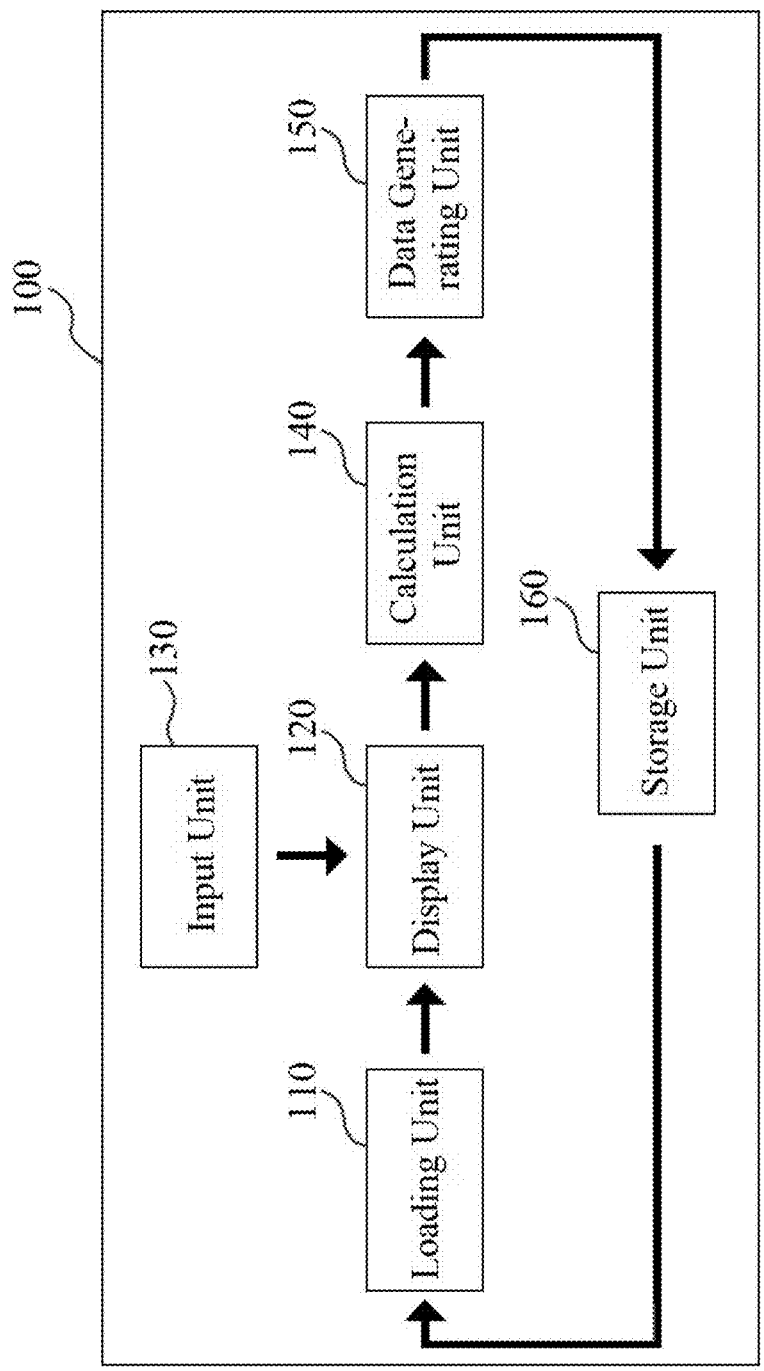
FIG. 3 shows an exemplary embodiment of a tooth separation system according to the disclosure.

FIG. 3 shows an exemplary embodiment of a tooth separation system 100 according to the disclosure.

The tooth separation system 100 can include a loading unit 110 for loading an intraoral scan data obtained by a CBCT for example, a display unit 120 for displaying the intraoral scan data loaded by the loading unit 110, an input unit 120 for making a tooth border mark onto each tooth shown on the display unit; a calculation unit 140 for performing necessary calculations to separate the tooth from the gums based on the tooth border mark; and a data generating unit 150 for generating a tooth model data from the intraoral scan data. The tooth separation system 100 may be a computing system, including but not limited to, a PC and a laptop computer. In addition, the tooth separation system 100 may further include a storage unit for storing the intraoral scan data and the tooth model data. This tooth separation system 100 may be used, as illustrated in FIG. 4.

FIG. 4 shows an exemplary embodiment of a method of using the tooth separation system according to the disclosure.

Figure 4A:
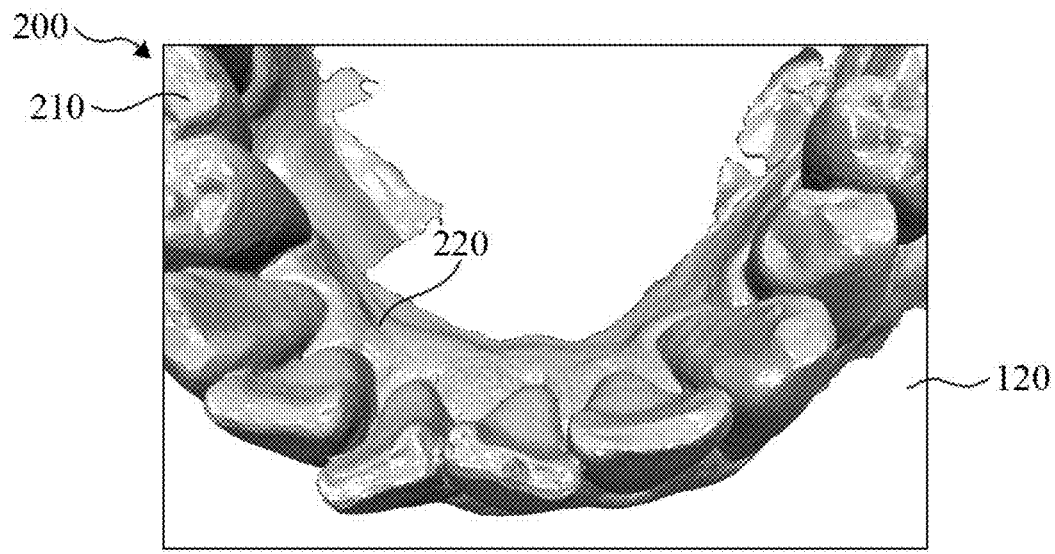
FIGS. 4A and 4B shows an exemplary embodiment of a method of using a tooth separation system according to the disclosure.
Figure 4B:
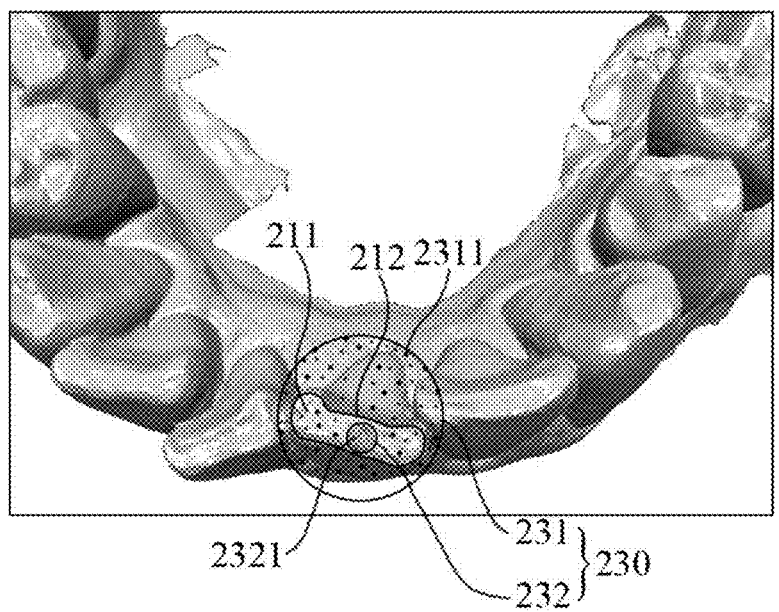

First, the loading unit 110 fetches the intraoral scan data from the storage unit 160, and the display unit 120 displays the data, as shown in FIG. 4A. While FIG. 4A illustrates the structure 200 of mandible teeth, the same method can be applied to the structure of maxillary teeth. The display unit 120 may be an LCD monitor, for example. The display unit 120 shows teeth 210 and gums 220 all together. The input unit 130 is used for making a tooth border mark 230 on each of the teeth 210, as shown in FIG. 4B. Examples of the input unit 130 may include but not limited to, a keyboard, a mouse, and so on. The tooth border mark 230 may comprise a larger circle 231 and a smaller circle 232 that fits inside the larger circle 231. The smaller circle 232 is defined on the top surface 211 of the tooth 210. In addition, the smaller circle 232 is preferably defined within the border 212 of the top surface 211 of the tooth 210 because the calculation unit 140 may fail to achieve a precise separation between the tooth 210 and the gum 220 if the smaller circle 232 is defined outside the border 212 of the top surface 211 of the tooth 210. More details on how to define the smaller circle 232 on the top surface 211 of the tooth 210 will be provided below with reference to FIG. 5. The larger circle 231 is defined outside the border 212 of the top surface 211 of the tooth. Preferably, the larger circle 231 should not go beyond the boundary of the top surface of a neighboring tooth. When a tooth border mark 230 is made on each of the teeth 210, a plurality of points 2311, 2321 is automatically plotted within the larger and smaller circles 231, 232. This plurality of points 2311, 2321 correspond to vertices of a mesh that configures the intraoral scan data. In other words, 3D intraoral scan data is composed of numerous meshes and contains information on vertices of the meshes. Having a tooth border marker 230 on each of the teeth, therefore, it becomes possible to automatically select a plurality of points 2311, 2321 inside the smaller and larger circles 232, 231. The calculation unit 140 then performs necessary calculations based on these automatically selected points 2321, 2311 inside the smaller circle 232 and between the larger circle 231 and the smaller circle 232, respectively, to allow a clear distinction between the teeth 210 and the gums 220. According to the underlying algorithm for the calculation unit 140 to distinguish the teeth 210 from the gums 220 in the scan data using the plurality of points 2311, 2321, first, a value of "1" is given to those points 2311 inside the smaller circle 232, and a value of "0" is given to those points located at the boundary of the larger circle 231 among the plurality of points 2321 inside the larger circle 231. Next, Laplace's equation is set up on mesh curved surfaces. In this case, a coefficient value is defined to each line connecting two points 2311, 2321, and a smaller value is given to those lines in the vicinity of a recessed surface such that a clear distinction is achieved between the teeth and the gums. By solving Laplace's equation, every point 2311 inside the larger circle 231 except for those points at the boundary of the larger circle 231 would have a real number between 0 and 1. These values are used for interpolation between the points 2321 that are inside the smaller circle 232 having a value of "1" and the points 2311 that are at the boundary of the larger circle 231 having a value of "0". Finally, any suitable real number between 0 and 1 is selected to calculate or extract an isoline on the mesh surface that serves as the boundary between the teeth and the gums. Such a real number used for extracting an isoline can be automatically selected through the use of mesh information. The calculation unit 140 may be a central processing unit (CPU), for example. Once the tooth 210 is separated from the gum 220 with the help of the calculation unit 140, the data generating unit 150 may use information on this separated tooth and generate tooth model data from the intraoral scan data. The tooth model data thus generated is then stored in the storage unit 160 to be loaded later when needed. While the tooth border mark 230 has a circular shape in this example, any suitable shape, including but not limited to, a rectangular shape, a triangular shape, or a polygonal shape, may be used within the scope of the disclosure. In other words, any shape, with one being larger and the other being smaller to fit inside the larger one, can be used for the tooth border mark 230.

Figure 5A:
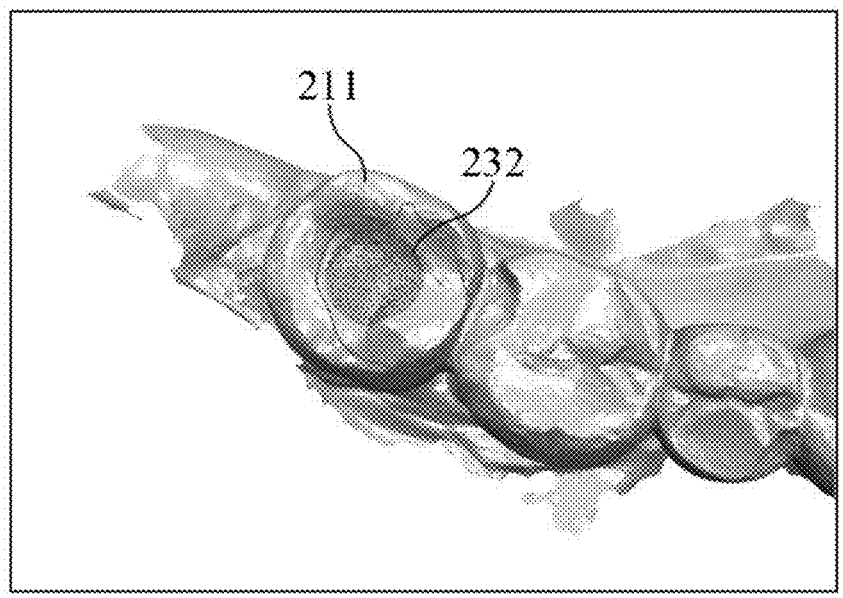
FIGS. 5A and 5B show another exemplary embodiment of a method of using a tooth separation system according to the disclosure.

FIG. 5 shows another exemplary embodiment of a method of using a tooth separation system according to the disclosure.

Figure 5B:
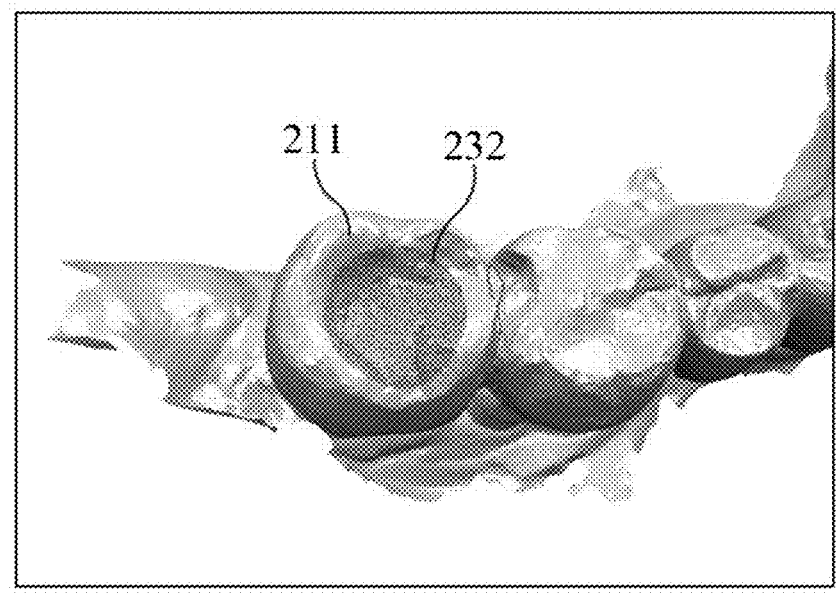

When there is a recessed portion on the top surface 211 of a tooth, the smaller circle 232 of the tooth border mark 230 is preferably defined to surround the recessed portion, as shown in FIG. 5B. This is because if the smaller circle 232 is smaller than the recessed portion, the calculation unit 140 may fail to achieve a precise separation between the tooth and the gum.

FIG. 6 shows yet another exemplary embodiment of a method of using a tooth separation system according to the disclosure.

Figure 6A:
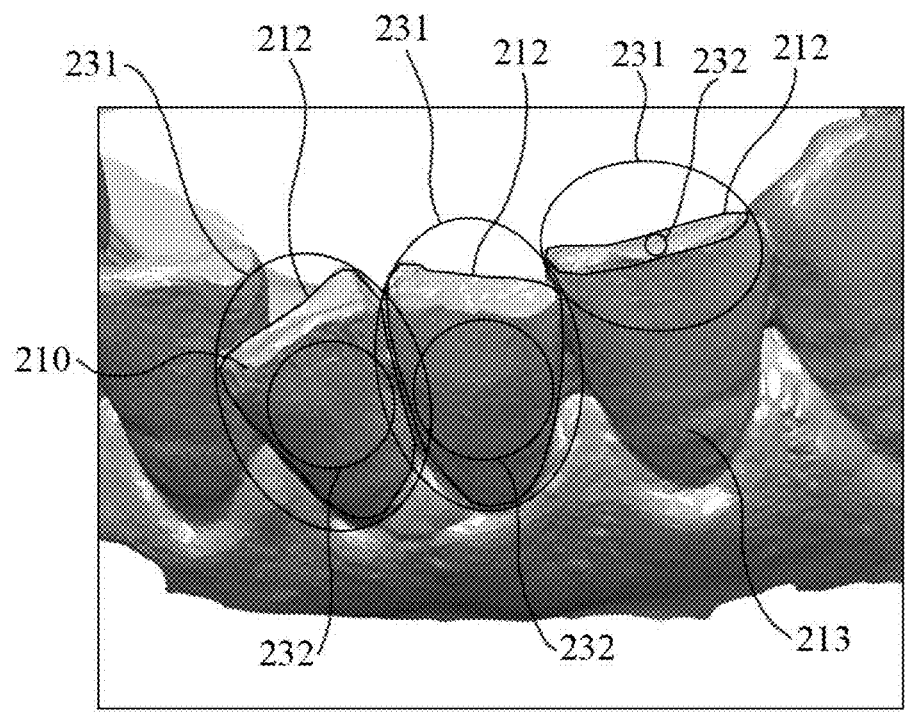
FIGS. 6A and 6B show yet another exemplary embodiment of a method of using a tooth separation system according to the disclosure.
Figure 6B:
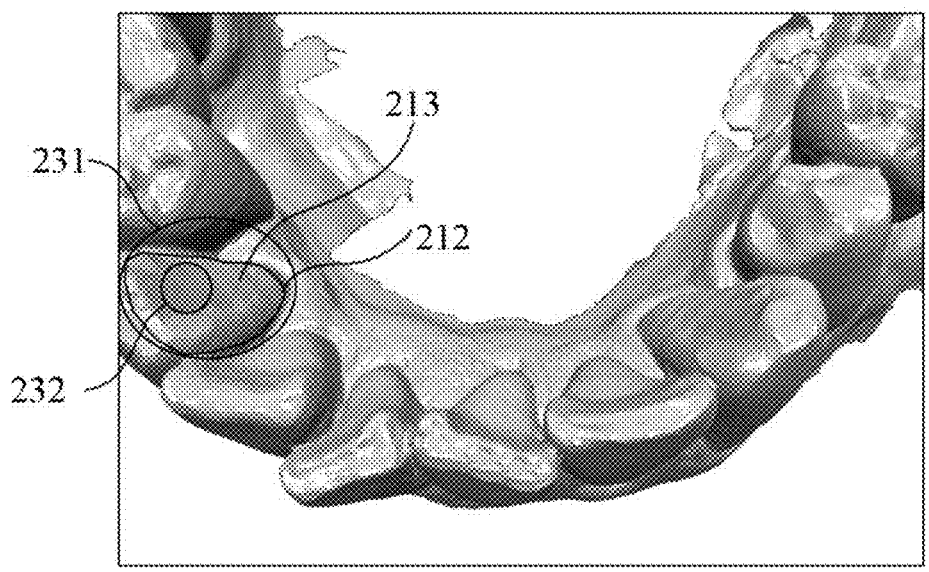

The smaller circle 232 of the tooth border mark 230 may be defined on the top surface as well as any other surfaces 213 of a tooth, as shown in FIGS. 6A and 6B. However, it is desirable that the smaller circle 232 would not be defined outside the border 212 of the tooth 210 including the surfaces 213 of the tooth. In addition, it is preferable that the smaller circle 232 is defined on an area of the upper surface of the tooth that has many recessed portions. In this case, it is preferable that the larger circle 231 is defined outside the border 212 of the tooth 210 including a surface 213 having the smaller circle 232 defined thereon.

FIG. 7 shows yet another exemplary embodiment of a method of using a tooth separation system according to the disclosure.

Figure 7A:
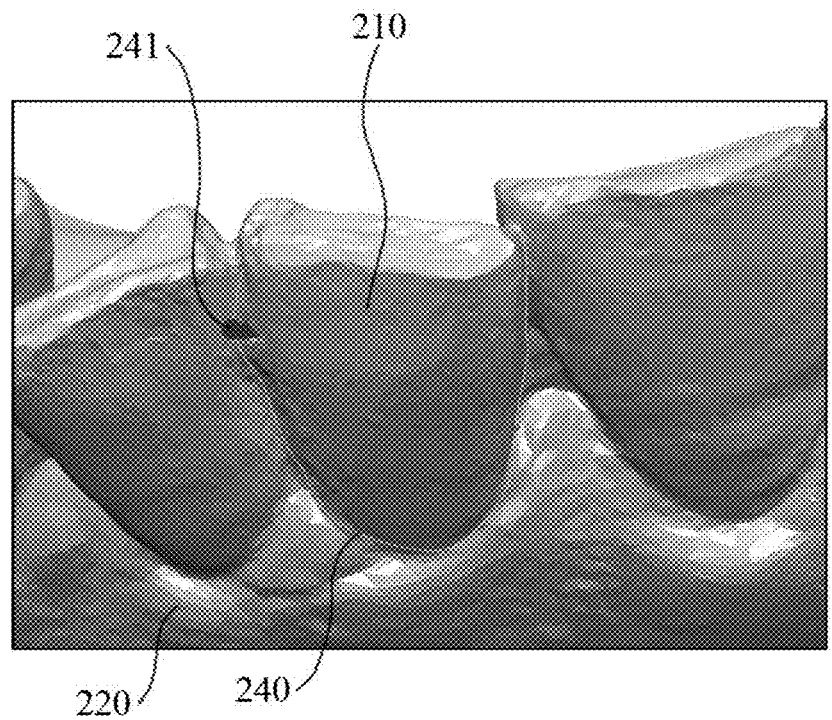
FIGS. 7A and 7B show yet another exemplary embodiment of a method of using a tooth separation system according to the disclosure.
Figure 7B:
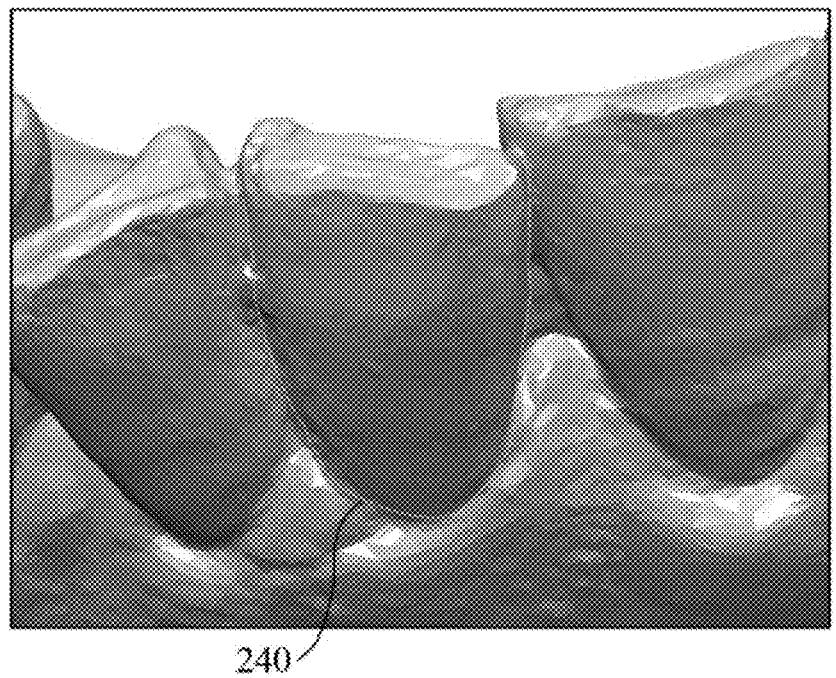

Referring to FIG. 7A, separation between the teeth 210 and the gums 220 achieved by the calculation unit may be indicated by a tooth boundary line 240 on the display unit. If the tooth boundary line 240 has accidentally invaded a portion 241 of a neighboring tooth as shown in FIG. 7A, the user may correct it by shifting the tooth boundary line 240 off the portion 241 through the input unit, such that the tooth boundary line may be drawn accurately without an error, as shown in FIG. 7B.

Set out below are clauses that describe diverse features of further aspects of the disclosure.

(1) A tooth separation system comprising: a loading unit for loading an intraoral scan data; a display unit for displaying the intraoral scan data loaded by the loading unit, in which the intraoral scan data includes a tooth as well as gums; an input unit for making a tooth border mark onto the tooth shown on the display unit; and a calculation unit for performing necessary calculations to separate the tooth from the gums based on the tooth border mark.

(2) The tooth separation system further comprising: a data generating unit for generating a tooth model data from the intraoral scan data, for the tooth separated from the gums by the calculation unit.

(3) The tooth separation system, wherein the tooth border mark comprises a larger shape and a smaller shape fit inside the larger shape.

(4) The tooth separation system, wherein the smaller shape is defined on a surface of the tooth.

(5) The tooth separation system, wherein for the surface of the tooth which has a recessed portion, the smaller shape is formed in a configuration that the recessed portion is surrounded by the smaller shape.

(6) The tooth separation system, wherein the smaller shape is defined within the border the surface of the tooth.

(7) The tooth separation system, wherein the larger shape is defined outside the border of the surface of the tooth.

(8) The tooth separation system, wherein the smaller shape is defined within the border of the top surface of the tooth, and the larger shape is defined outside the border of the top surface of the tooth.

(9) The tooth separation system, wherein the calculation unit separates the tooth from the gums based on a plurality of points plotted within the smaller shape and a plurality of points plotted between the smaller shape and the larger shape.

(10) A tooth separation method comprising: loading, by a loading unit, an intraoral scan data; displaying, by a display unit, a tooth as well as gums according to the intraoral scan data; making, by an input unit, a tooth border mark onto the tooth shown on the display unit; and performing necessary calculations, by a calculation unit, so as to separate the tooth from the gums based on the tooth border marks.

(11) The tooth separation method, wherein the tooth border mark comprises a larger shape and a smaller shape fit inside the larger shape.

(12) The tooth separation method, wherein the smaller shape is defined within the border of the surface of the tooth, and the larger shape is defined outside the border of the surface of the tooth.

The tooth separation systems and methods according to the disclosure allow the user to be able to make a precise separation between teeth and gums, without much difficulty in the use of such systems.

What is claimed is:

1. A tooth separation system comprising:
    a loading unit is configured to load an intraoral scan data;
    a display unit is configured to display the intraoral scan data loaded by the loading unit, in which the intraoral scan data includes a tooth as well as gums;
    an input unit is configured to make a tooth border mark onto the tooth shown on the display unit; and
    a calculation unit is configured to perform necessary calculations to separate the tooth from the gums based on the tooth border mark, wherein:
    the tooth border mark comprises a larger shape and a smaller shape fit inside the larger shape;
    each of the larger shape and the smaller shape is a closed curve;
    a plurality of points is automatically plotted within the larger shape and the smaller shape; and
    the calculation unit is configured to separate the tooth from the gums based on the plurality of points plotted within the smaller shape and the plurality of points plotted between the smaller shape and the larger shape.

2. The tooth separation system according to claim 1 further comprising a data generating unit is configured to generate a tooth model data from the intraoral scan data, for the tooth separated from the gums by the calculation unit.

3. The tooth separation system according to claim 1, wherein the smaller shape is defined on a surface of the tooth.

4. The tooth separation system according to claim 3, wherein for the surface of the tooth which has a recessed portion, the smaller shape is formed in a configuration that the recessed portion is surrounded by the smaller shape.

5. The tooth separation system according to claim 3, wherein the smaller shape is defined within the border the surface of the tooth.

6. The tooth separation system according to claim 1, wherein the larger shape is defined outside the border of a surface of the tooth.

7. The tooth separation system according to claim 1, wherein the smaller shape is defined within the border of a top surface of the tooth, and the larger shape is defined outside the border of the top surface of the tooth.

\* \* \* \* \*